United States Patent [19]
Sabins et al.

[11] Patent Number: 5,992,223
[45] Date of Patent: Nov. 30, 1999

[54] ACOUSTIC METHOD FOR DETERMINING THE STATIC GEL STRENGTH OF A CEMENT SLURRY

[75] Inventors: Fred L. Sabins, Missouri City; Voldi Maki, Austin, both of Tex.

[73] Assignee: Chandler Engineering Company LLC, Broken Arrow, Okla.

[21] Appl. No.: 08/947,691

[22] Filed: Oct. 9, 1997

Related U.S. Application Data

[60] Provisional application No. 60/052,406, Jul. 14, 1997.

[51] Int. Cl.$^6$ ............................ G01N 29/02; G01N 33/38
[52] U.S. Cl. ........................................ 73/64.42; 73/54.03
[58] Field of Search ............................. 73/54.03, 54.41, 73/61.49, 64.42, 64.53, 599, 597

[56] References Cited

U.S. PATENT DOCUMENTS

| | | |
|---|---|---|
| 2,833,142 | 5/1958 | Runquist et al. . |
| 3,641,811 | 2/1972 | Gnaedinger, Jr. et al. . |
| 4,259,868 | 4/1981 | Rao et al. . |
| 4,265,120 | 5/1981 | Morris et al. . |
| 4,377,087 | 3/1983 | Rodot . |
| 4,567,765 | 2/1986 | Rao et al. . |
| 4,622,846 | 11/1986 | Moon et al. . |
| 4,649,750 | 3/1987 | Cantrell et al. . |
| 4,655,084 | 4/1987 | Renzel . |
| 4,754,645 | 7/1988 | Piche et al. . |
| 4,862,384 | 8/1989 | Bujard . |
| 5,009,102 | 4/1991 | Afromowitz . |

(List continued on next page.)

FOREIGN PATENT DOCUMENTS

| | | |
|---|---|---|
| 0 577 511 | 1/1994 | European Pat. Off. . |
| 196 25 111 | 10/1997 | Germany . |

OTHER PUBLICATIONS

"Ultrasonic Characterization of a polymerizing epoxy resin with imbalanced stoichiometry", Marni Matsukawa and Isao Nagai, *J. Accoust. Soc. Am.*, vol. 99, No. 4, Pt. 1, Apr. 1996.

"The Relationship of Thickening Time, Gel Strength, and Compressive Strengths of Oilwell Cements,"SPE 11205, Sabins and Sutton, 1982, presented Sep. 25–29, 1992, Society of Petroleum Engineers, 57th Annual Fall Conference.

"Here's how to apply laboratory cement–test specifications to actual operations," Sabins, et al., *Oil and Gas Journal*, May 23, 1983.

The Effect of Excessive Retardation on the Physical Properties of Cement Slurries, Sabins, et al. Presented Oct. 5–7, 1981, Society of Petroleum Engineers 56th Conference.

"Interrelationship Between Critical Cement Properties and Volume Changes During Cement Setting," Sabins, et al, SPE 20451, presented 65th Annual Conference of the Society of Petroleum Engineers, Sep. 23–26, 1990.

"Transition Time of Cement Slurries Between The Fluid and Set State," Sabins et al., Presented at the 55th Annual Fall Technical Conference, Society of Petroleum Engineers, Sep. 21–24, 1980.

"New Technology in Gas Migration Control," Sykes, et al., Presented at the 62nd Annual Conference, Society of Petroleum Engineers, Sep. 27–30, 1987.

Sayers C M et al.: "Ultrasonic Propagation Through Hydrating Cements"; Ultrasonics; vol. 31, No. 3, Jan. 01, 1993, pp. 147–153; XP00065295.

*Primary Examiner*—Michael Brock
*Attorney, Agent, or Firm*—Fellers, Snider, Blankenship, Bailey & Tippens, P.C.

[57] ABSTRACT

An acoustic method and system for determining the static gel strength of one or more cement slurry samples at wellbore temperatures and pressures. The cement slurry sample to be tested is maintained in a static condition inside an acoustic pressure vessel at a controlled temperature and pressure. A first transducer generates an acoustic signal which is transmitted through the sample. A second transducer measures and records the amplitude of the acoustic signal after it transits the sample. This data is then processed and the static gel strength of the sample is determined according to a predetermined relationship relating signal amplitude to static gel strength.

19 Claims, 6 Drawing Sheets

U.S. PATENT DOCUMENTS

| | | |
|---|---|---|
| 5,092,176 | 3/1992 | Buttram et al. . |
| 5,099,849 | 3/1992 | Rossman et al. . |
| 5,119,820 | 6/1992 | Rossman et al. . |
| 5,412,990 | 5/1995 | D'Angelo et al. ........................ 73/597 |
| 5,433,112 | 7/1995 | Piche et al. . |
| 5,741,971 | 4/1998 | Lacy . |

ACOUSTIC METHOD FOR DETERMINING THE STATIC GEL STRENGTH OF A CEMENT SLURRY

CROSS REFERENCE TO RELATED APPLICATION

This application claims the benefit of copending U.S. provisional application Ser. No. 60/052,406 filed Jul. 14, 1997.

BACKGROUND OF THE INVENTION

1. Technical Field

This invention relates generally to a method and system for testing oil well cement samples, and, more specifically, to non-mechanically estimating the static gel strength of a cement slurry by measuring changes in the amplitude of an acoustic signal transmitted through the slurry under typical wellbore temperature and pressure conditions and correlating the measured signal attenuation data to actual static gel strength measurements.

2. Background

Most cement slurry formulations used in cementing oil, gas and geothermal wells are first tested for specific cement slurry properties conducted in a cement testing laboratory. To be meaningful, tests must simulate actual job conditions. Many aspects of oil well cementing are important, but the cement formulation is one of the few items which can be changed to modify the slurry performance under existing well conditions. The cement slurry is one of the most tested components pumped into a well.

The basic design of a cement slurry starts with determining what general properties are needed for predicted well conditions. The fracture or parting pressure of the weakest formation and cement column height determines maximum density of the cement slurry. The zone with the highest gas pressure gradient determines minimum density. The difference in the hydrostatic pressure and the highest formation pressure is the critical parameter that affects the cement slurry's ability to control the formation fluid flow into the cement column and is referred to as "overbalanced pressure". A low overbalanced pressure will require the cement slurry to have increased compressibility, early plastic state expansion, fluid loss control, modified gel strength profile, or possibly a complete change in job procedure. Other downhole parameters like salt zones and sensitive shales call for special additives to the slurry. Except for highly unusual situations, slurry specifications are met simply by additive selection based on previous experience or laboratory test results.

With the basic slurry formulation established, two physical properties of the slurry are of initial concern. The cement must remain fluid long enough to be pumped to its desired location downhole. Also, once the cement is in place it must set and develop an adequate compressive strength value within a specific time period. Thickening time tests and compressive strength tests account for most of the analysis conducted on cement slurries in field laboratories.

Thickening time measurements are generally determined using a high temperature-high pressure (HTHP) consistometer. This apparatus consists essentially of a rotating cylindrical slurry container equipped with a stationary paddle assembly, all enclosed in a pressure chamber capable of withstanding a pressure of 207 MPa (30,000 psi) and maximum temperatures to 204° C. (400° F.). A heating element is used to affect the temperature of the slurry at a maximum rate of 2.8° C. (5° F.)/minute. The thickness or consistency of the cement slurry is monitored by measuring the torque on the stationary stirring paddle and correlating the measured torque to amount of fluid time available for pumping the cement slurry.

Compressive strength measurements are best taken using what is known as the Ultrasonic Cement Analyzer (UCA). The UCA was developed to measure the compressive strength of a cement slurry as it sets when subjected to simulated oil field temperatures and pressures. It consists of a high temperature-high pressure autoclave, a heat jacket capable of heating rates up to 5.6° C. (10° F.) per minute, a pair of 400 kHz ultrasonic transducers for measuring the transit time of an acoustic signal transmitted through the slurry, plus associated hydraulic plumbing. The two transducers make transit time measurements through the cement as it sets. A short pulse on a lower transducer propagates through the cement to an upper transducer. Set time and compressive strength are calculated from measured transit time via empirically developed equations. U.S. Pat. Nos. 4,259,868 and 4,567,765 disclose the UCA in detail and are incorporated herein by reference.

Unfortunately thickening time tests and compressive strength tests do not tell the whole story. Thickening time is a test which only simulates actual job conditions up to the predicted placement time. After allowing for test accuracy variation, a thickening time longer than the placement time allows for some margin of safety but only for continuous pumping at a lower than predicted rate. Thickening time "safety factors" do not directly relate to how long a slurry can remain static and still be moved after an inadvertent or intentional shutdown during placement. With respect to what actually takes place downhole, a thickening time measurement provides information on what happens up to the end of placement time. A thickening time of six hours tells nothing about what change will occur when the slurry is allowed to remain static after pumping. The compressive strength test shows the degree of hydration and set that will occur 8, 12 or 24 hours after placement. Until recently, the in-between period was left to speculation.

An important phenomenon occurring in the cement slurry after it has been pumped downhole is static gel strength development. Static gel strength development is a by-product of the initial hydration process of the cement. The beginning of gel strength development signals the point at which the cement slurry starts its change from a true hydraulic fluid which transmits full hydrostatic pressure to a solid set material that has measurable compressive strength. This period of change is called the transition phase. During the transition phase the cement slurry is continually gaining gel strength. This gel strength is important for two reasons. First the static gel strength development determines the shut down safety factor on the job. If the cement slurry is stopped prior to placement then the gel strength allows the calculation of the pressure required to restart circulation. Secondly the static gel strength affects the pressure reduction and the fluid flow of gas or water into the cement filled annulus. This fluid flow problem will be the main focus of the static gel strength discussion due to its importance.

Static gel strength in the cement enables a potential pressure restriction to occur in a cement filled annulus. If volume decreases occur when gel strengths are present, the actual pore pressure in the cement can decrease. This pressure decrease can be severe enough to allow gas to enter the annulus. The total time of this transition period is critical when gas flow potential exists. If the transition time becomes longer, it allows more volume decreases to occur, and thus, more gas flow into the cement column. If the gel strength in the cement slurry is high enough and the fluid volume low enough then migration of gas is prevented.

In addition to gas flows through a cement slurry many in the industry are using static gel properties to control the flow of water. Some believe water flows through cement slurries to be the most critical problem encountered while drilling, for example, in deep water in the Gulf of Mexico. Static gel strength development can be quantified and utilized to design slurries that prevent undesirable water flow.

The next important phenomena that occurs after pumping and the onset of static gel strength development is set time. This is the point where compressive strength first begins to develop in the cement slurry. This signals the end of static gel strength development and the start of compressive strength development and will determine what is called the waiting-on-cement (WOC) time.

The present invention is primarily concerned with new methods and apparatus for determining the static gel strength characteristics of cement slurries.

Static gel strength (SGS) is basically a shear bond strength measurement derived from the pressure required to move a gelled fluid through a pipe or annulus at a micro rate. The unit compatible equation, $$SGS = P(D/4L)$$

(or)

$$P = SGS \times 4(L/D)$$

is in fact a definition of static gel strength, as well as an application equation. The units of SGS in USA engineering units are lbs./100 ft$^2$ when derived from the equation SGS= 300 P×D/L where P (pressure)=psi, D (effective diameter, hole size minus the pipe size)=in. and L (length)=ft.

Different measurement systems have heretofore been employed for determining static gel strength. In one system a device similar to a consistometer is specifically designed for measuring static gel strength after a stirring period to simulate slurry placement. The equipment is designed to simulate downhole conditions and a low friction magnetic drive allows the slurry to be stirred while monitoring consistency during the stirring time. After simulating placement time, the motor is shutoff and a cord pulling system is attached to the magnetic drive head. Static gel strength is determined by continuously measuring the torque required to rotate a paddle at a very slow speed (0.5 to 2.0 degrees per minute). At such speeds, a magnetic drive has very low friction and accurate torque measurements can be made. In this system the torque measuring equipment consists of a cord pulling capstan or drum arrangement driven by a variable speed gear motor with the cord running through the pulley arrangement to a load cell and then to the magnetic drive of the stirring autoclave. This provides a method of accurate continuous rotation and a means for continuously recording the torque. The gel strength is then calculated from the torque measurement and the paddle geometry. The slow movement of the paddle allows static gel strength to be measured but does not inhibit gel strength development. With this device gel strength properties can be measured from a minimum of 4.8 Pa (10 lbs./100 ft$^2$) up to a maximum of 480 Pa (1000 lbs./100 ft$^2$). The well known Halliburton MACS analyzer is an example of this type of device.

Static gel strength has also been measured by determining the pressure drop across a length of tubing. The basic set-up of such an apparatus allows for the circulation of the test slurry through a small diameter tubing. After placement, the slurry is pressurized with water to the test pressure. A sensitive pressure drop transducer measures the pressure drop of the cement as it gels from the entrance to the exit of the tubing. As the cement gels, a corresponding pressure drop will be observed. The pressure drop and the static gel strength can be related using the above equations.

Static gel strength has also been determined with a shearometer device. This device is a thin wall cylinder that is placed in a sample of the cement slurry and allowed to remain static for a period of time. Weight is then applied to the top of the tube until the tube moves through the cement slurry. This method is conducted at atmospheric pressure but at temperature if the temperature is less than 200° F.

One problem with prior art systems for determining SGS is that mechanical methods have a limited low-range torque measurement resolution and poor sensitivity. Mechanical methods and systems are also difficult to calibrate. Furthermore, tests such as the rotating paddle test may not provide a continuous measurement of SGS. In order to measure the static gel the gel is broken and only one data point is obtained.

While more accurate than a mechanical approach, pressure drop measurements of SGS as described above are not practical in most cases as it is difficult to analyze a large number of samples. Once a measurement is completed the tube is discarded and another is used for the next measurement. This is overly time consuming and expensive.

Tests such as the shearometer conducted at atmospheric pressure do not translate well to the characteristics of the cement slurries at downhole conditions (downhole pressure).

It is thus an object of the present invention to provide a non-mechanical method and apparatus for accurately determining the SGS of a cement slurry that increases the resolution and sensitivity of the measurement and provides a continuous measurement of SGS under downhole conditions.

It is another object of the invention that multiple samples of cement slurries be quickly and easily analyzed without undue expense.

SUMMARY OF THE INVENTION

The present invention arises from the discovery that as a cement slurry develops static gel strength the amplitude of an acoustic signal transmitted through the slurry also increases and the change in amplitude of such a signal correlates very well with the actual static gel strength of the slurry. Utilizing this discovery, an acoustic method and system for determining the static gel strength of a cement slurry sample was developed that provides for continuous, accurate, non-mechanical measurements of the static gel strength of multiple cement slurry samples. The measurements are quickly and easily made at wellbore temperatures and pressures.

The cement slurry sample to be tested is maintained in a static condition inside an acoustic pressure vessel at a controlled temperature and pressure. A first transducer generates an acoustic signal which is transmitted through the sample. A second transducer measures and records the amplitude of the acoustic signal after it transits the sample. This data is then processed and the static gel strength of the sample is determined according to a predetermined relationship relating signal amplitude to static gel strength.

In accordance with one preferred aspect of the invention, the acoustic signal is an ultrasonic signal, and, more specifically, a high-frequency signal in the range of about 100–600 kHz. In one embodiment the signal is filtered with a filter centered at 500 kHz to eliminate all frequencies outside the desired frequency range.

In accordance with another preferred aspect of the invention, the acoustic signal is pulsed over time and the signal is repetitively measured to obtain a time history of the static gel strength of the sample. The observed static gel strength may also be compared to an arbitrary value and the time determined when such arbitrary value is achieved. For example, the arbitrary value may represent the point at which signal amplitude begins to increase which marks the onset of static gel strength. The arbitrary value may also represent the point at which the rate of increase in signal amplitude reaches a maximum, which indicates a specific high static gel strength.

In accordance with another preferred aspect of the invention, multiple cement slurry samples are simultaneously tested and the signal amplitude data obtained is processed by a single data processor which determines the static gel strength of the samples.

In accordance with another preferred aspect of the invention, the time required for the acoustic signal to transit the sample is measured simultaneously with the measuring of the amplitude and the compressive strength of the sample is concomitantly determined by using a known predetermined relationship.

A better understanding of the invention and its objects and advantages will become apparent to those skilled in this art from the following detailed description, taken in conjunction with the attached drawings, wherein there is shown and described only the preferred embodiment of the invention, simply by way of illustration of the best mode contemplated for carrying out the invention. As will be realized, the invention is capable of modifications in various obvious respects, all without departing from the invention. Accordingly, the description should be regarded as illustrative in nature and not as restrictive.

DETAILED DESCRIPTION OF THE PREFERRED EMBODIMENT

Data from amplitude and travel time measurements made using a modified UCA indicate that there is a property change in a cement slurry that is measurable prior to the initial set. This property change that is occurring prior to initial set is in fact the static gel strength. Data from amplitude and travel time measurements demonstrated that the gel strength of the cement slurry can be observed. The amplitude of an acoustic signal passed through a cement slurry sample was found to increase prior to initial set. In addition, the change in the amplitude of the high frequency signal was discovered to correlate very well with the actual static gel strength obtained by known methods. Thus, it was determined that this amplitude measurement alone may be used to predict the static gel strength of the cement slurry sample.

Figure 1:
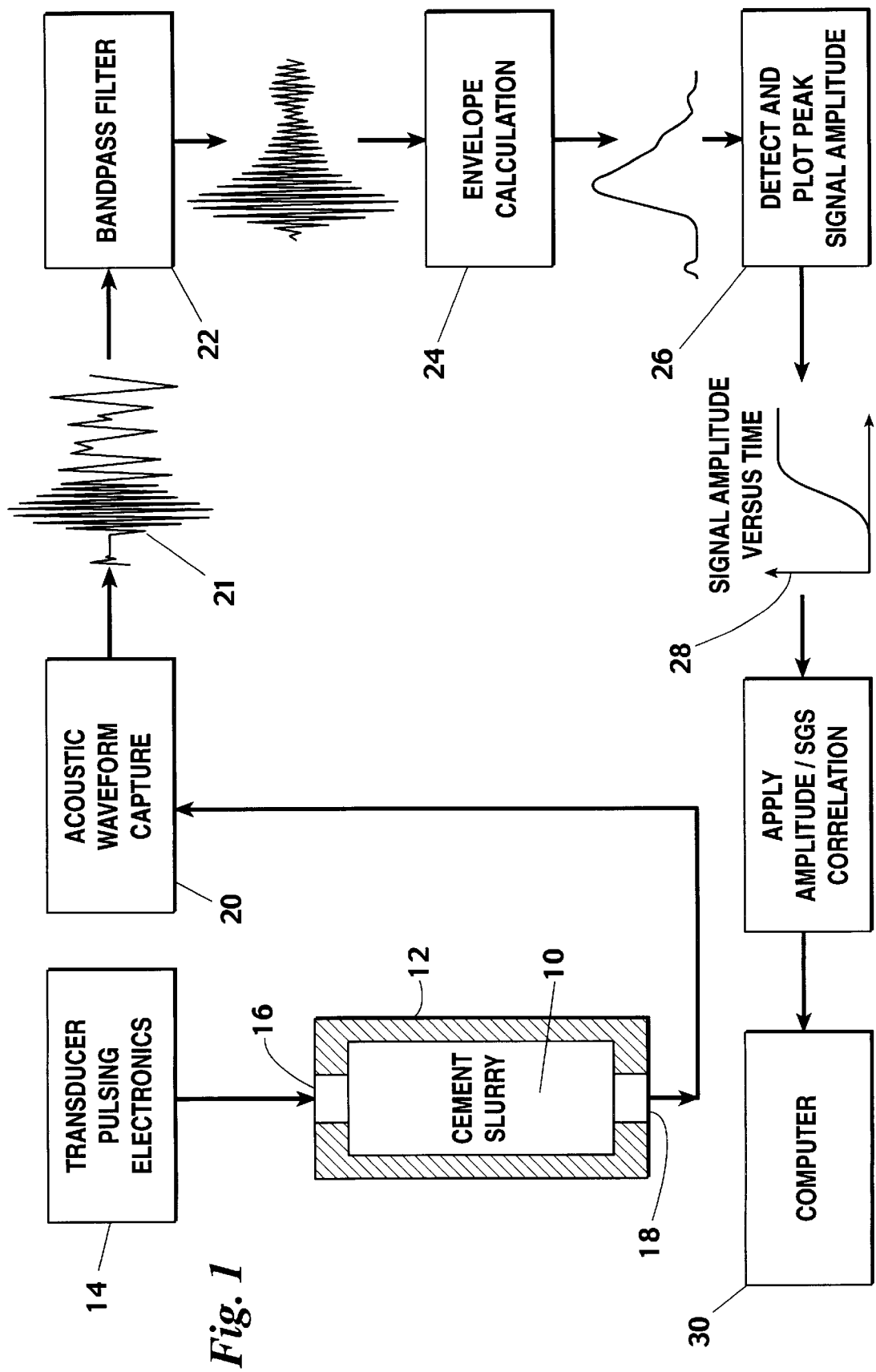
FIG. 1 is a flow diagram demonstrating the preferred embodiment of the present invention.

The present invention generally involves measuring the amplitude of an acoustic signal as it transits a cement slurry sample and correlating the signal amplitude to static gel strength. Referring first to FIG. 1, a cement slurry sample 10 is deposited into an acoustic pressure vessel 12. There the temperature and pressure can be controlled so as to maintain the cement slurry sample 10 in a static state simulating wellbore conditions. Transducer pulsing electronics 14 are used to generate the acoustic signal. A first transducer 16 located at one end of the pressure vessel 12 transmits the acoustic signal through the sample to a second or receiving transducer 18. A signal analogous to the acoustic waveform is then captured and digitized with electronics 20.

As represented in FIG. 1, the captured acoustic waveform 21 is filtered 22 with a bandpass filter to obtain the preferred high frequency ultrasonic signal in the range of 100–600 kHz. An envelope calculation 24 is then performed on the filtered waveform and the peak amplitude of the pulsed signal is plotted 26 to generate a graphical representation of signal amplitude versus time 28. The static gel strength of the sample 10 is then calculated by a data processor, such as a computer 30, according to a predetermined relationship correlating signal amplitude to static gel strength.

Measurements may be made using a modified UCA. The conventional UCA uses two transducers to make transit time measurements through a cement slurry sample as it sets. A short pulse on a first transducer propagates through the sample to the second transducer. The time of arrival of the pulse is used to calculate the compressive strength of the cement. Reference is made again to U.S. Pat. Nos. 4,259,868 and 4,567,765, previously incorporated herein by reference, which disclose the conventional UCA in detail including suitable acoustic pressure vessels. The measurements used in connection with the present invention are obtained by digitizing the signal received from the conventional UCA and using various processing algorithms to measure the character of the acoustic signal so as to relate them to the static gel strength of the cement.

Figure 2:
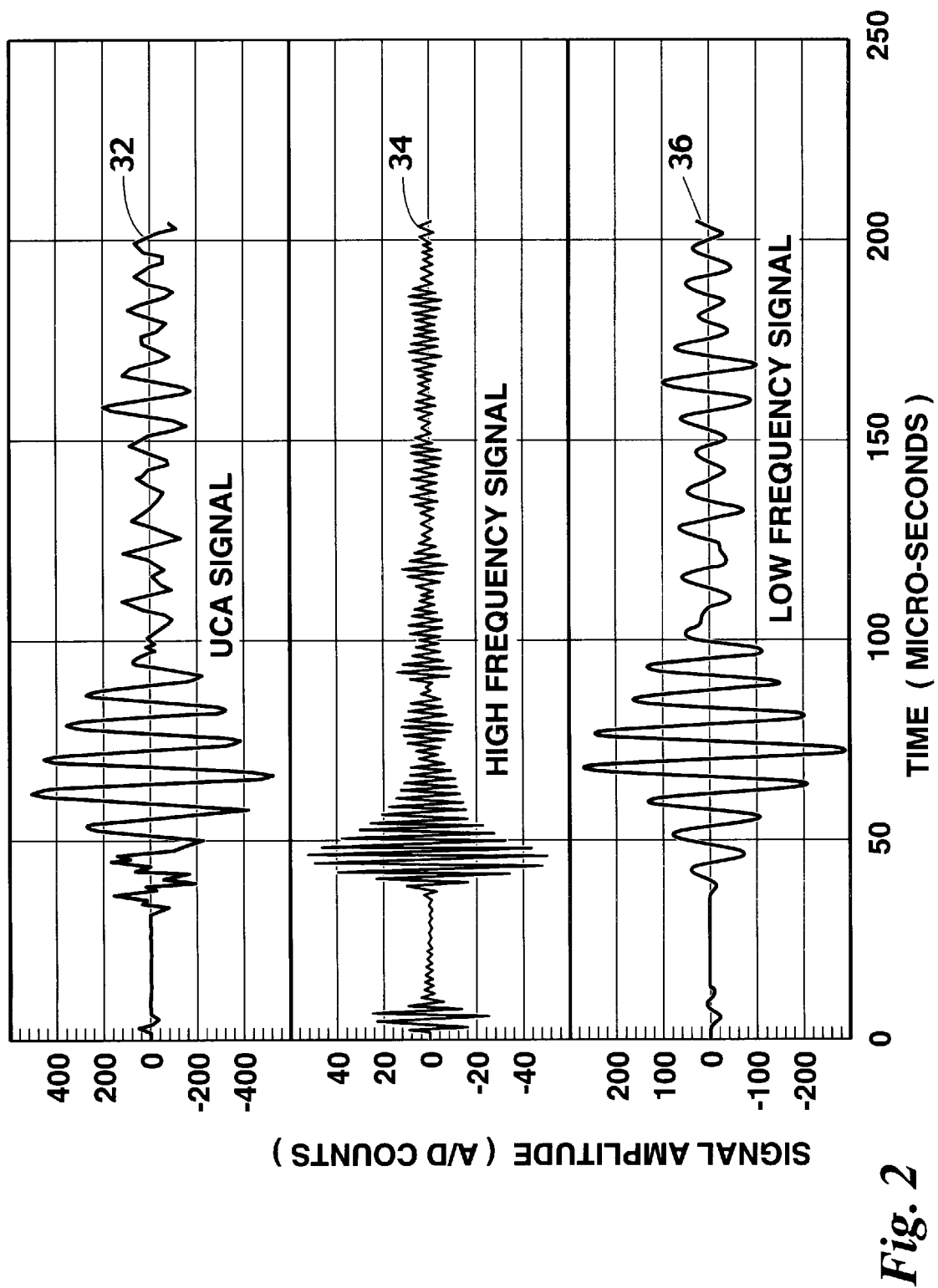
FIG. 2 shows three traces of a typical acoustic signal transmitted through a cement slurry sample.

Typical processing signals are shown in FIG. 2. The upper trace 32 shows a signal which is processed by the electronics of the conventional UCA. Close examination shows that the signal consists of two major frequencies, one at approximately the thickness resonance of the transducer, and another at a much lower frequency. The middle trace 34 in FIG. 2 shows the high frequency signal filtered from the upper trace 32. The lower trace 36 shows the low frequency signal from the upper trace 32. The low frequency signal is much higher in amplitude than the high frequency signal. The conventional UCA measures the time when the signal exceeds some threshold without noting the amplitude.

Figure 3:
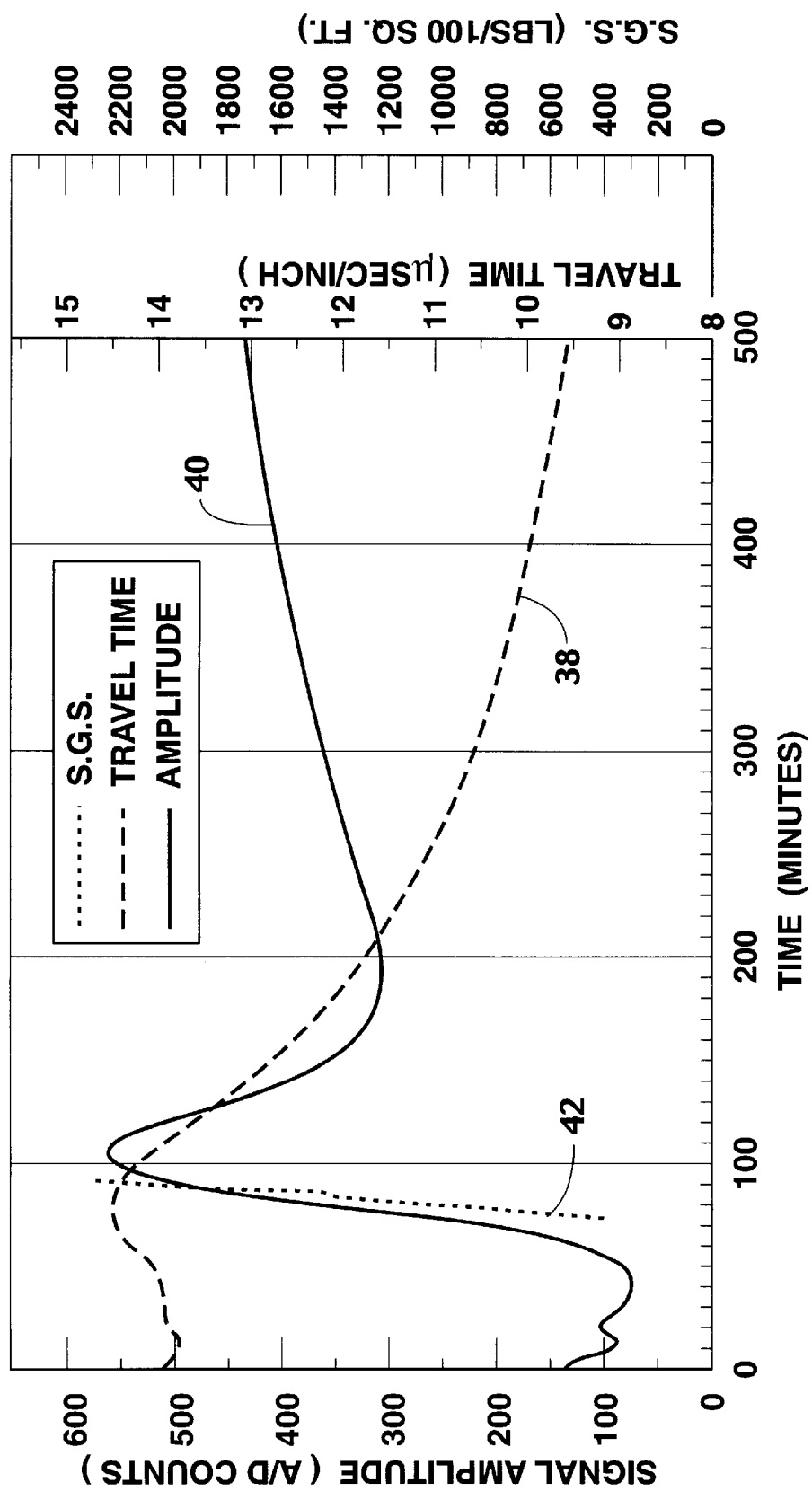
FIG. 3 shows travel time and amplitude data obtained from a typical sample of tested cement.

In the present invention the high frequency signal is preferably filtered from the UCA signal for subsequent processing and correlation to static gel strength. In practice the acoustic signal is filtered with a filter centered at 500 kHz to eliminate all frequencies outside the desired frequency range. FIG. 3 shows the travel time and amplitude data obtained from a typical sample of tested cement. The travel time is plotted in the dashed line 38. The travel time is relatively constant for a period of time, then increases and then decreases as the cement sets. The conventional UCA correlates this travel time information with the compressive strength of the cement. The amplitude of the acoustic signal is denoted in FIG. 3 by the solid line 40. The amplitude initially drops to a minimum. It then increases dramatically becoming a maximum shortly after travel time beings to decrease.

FIG. 3 also provides a graphical representation of the actual static gel strength 42 as compared to the captured acoustic waveform illustrating the relationship between static gel strength and signal amplitude. This graphical relationship represents the results of a number of tests conducted on several key cement slurries. Signal amplitude was obtained and correlated with static gel strength determinations derived from pressure drop and shearometer devices. The relationship between signal amplitude and static gel strength may be expressed by one or more algorithms used to program a computer or data processor to perform static gel strength determinations using captured signal amplitude. The computer or processor may be programmed to utilize algorithms representing graphical relationships derived for specific cement compositions or generalized graphical relationships obtained by an averaging of multiple samples.

Data processing may include comparing the static gel strength of a sample to an arbitrary value and determining the time when the static gel strength reaches the arbitrary value. In one aspect of the invention, the arbitrary value represents the point at which signal amplitude begins to increase, i.e. the low point or minimum value, which corresponds to the onset of static gel strength development. In another aspect of the invention, the arbitrary value represents the point at which the derivative of the signal ceases to increase, i.e. the inflection point or maximum value, which corresponds to the time of a specific static gel strength. This gel strength typically corresponds to initial set determined by the travel time measurement.

It should be noted that reference data was obtained to confirm that temperature and pressure changes within the acoustic pressure vessel will not adversely affect ability to correlate signal attenuation to static gel strength.

Figure 4:
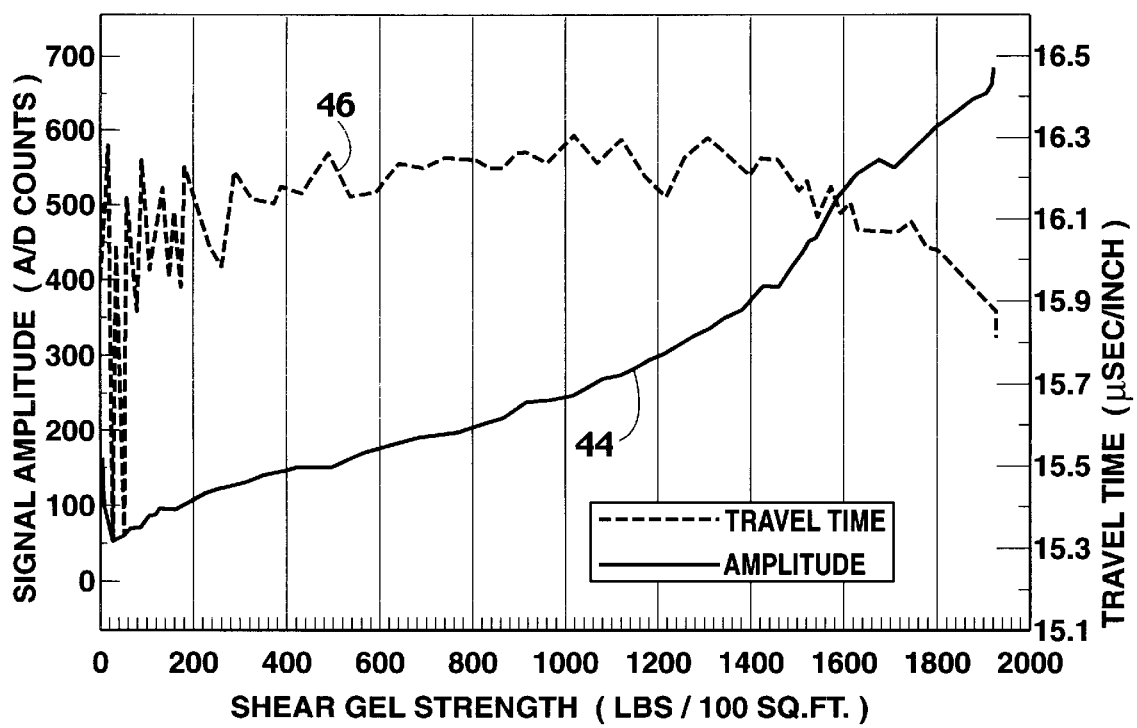
FIG. 4 shows a typical cross plot of travel time and amplitude versus static gel strength.

To determine the correlation of gel strength to the amplitude and travel time a cross plot is utilized to graphically demonstrate the relationships of the data. In the cross plot, the travel time and the amplitude are used as the y axis of a graph and the gel strength is used as the x axis. A typical cross plot is illustrated in FIG. 4 with the amplitude indicated by the solid line 44 and the travel time denoted by the dotted line 46. The amplitude shows a linear relationship from about 75 lbs./100 ft$^2$ to 1400 lbs./100 ft$^2$ gel strength. This confirms a direct linear relationship between the amplitude and the gel strength. The travel time shows some trend to increase while the gel strength increases, but using the travel time to predict gel strength would not produce an accurate estimate of the gel strength. In the cements tested, the amplitude consistently matched the development of the gel strength of the cement. The travel time occasionally tracked the gel strength, but just as often did not.

The present invention may be practiced with a modified UCA. The electronics are designed specifically to maximize the accuracy of the necessary measurements. The computer 30 (FIG. 1) controls measurement command and retrieval of travel time and amplitude data.

Figure 5:
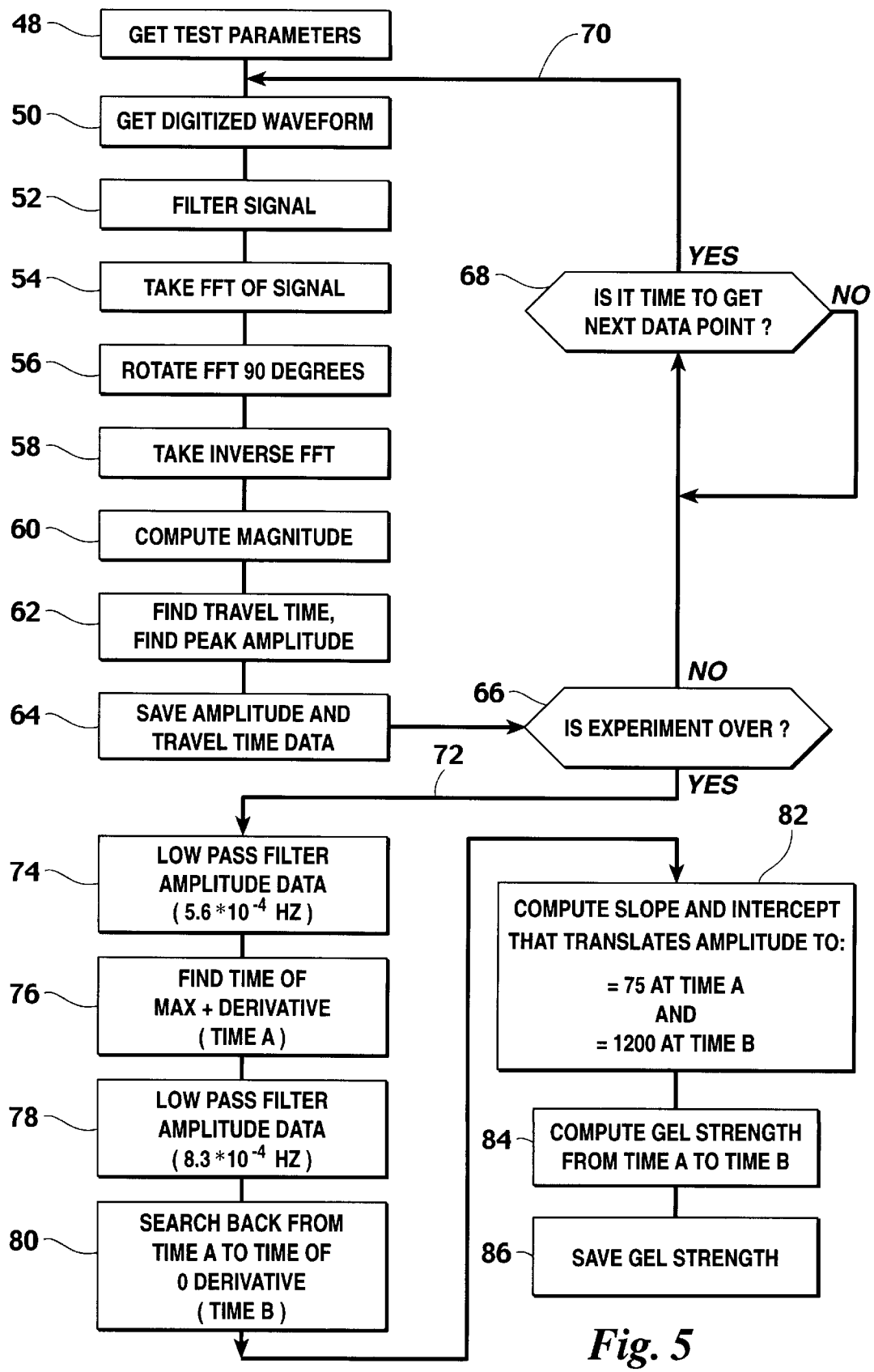
FIG. 5 is a flow diagram of a reading program for processed data.

A block diagram of a program for computer 30 for use in connection with the modified UCA is shown in FIG. 5 with the program steps indicated by reference numerals. The operator first inputs test parameters 48 such as the duration of the test and the sample period of the instrument. Typically the test would be run for 24 hours and the condition of the cement would be sampled once every 2 minutes. The first transducer (14 FIG. 1) generates an acoustic pulse and the signal received by the second transducer (18 FIG.1) is digitized 50. The digitized signal is filtered 52 to remove frequencies above and below the center frequency of the measurement. The signal is then transformed 54 into the frequency domain using a standard FFT routine. This signal is thenrotated 90 degrees 56. The inverse FFT is taken 58 to produce the imaginary component of the signal. The envelope or magnitude is computed 60 by taking the square root of the sum of the squares of the real and imaginary components of the signal at each sample point. The travel time may now be found 62 as well as the amplitude of the pulse of acoustic energy which propagates through the cement. These two data points are stored 64 to process the gel strength and compressive strength of the cement. The computer then checks 66 to see if the test is complete. If it is not it then checks 68 to see if it is time to take the next sample. If it is not yet time, the computer keeps checking until it is time. It then loops back 70 to take another waveform sample and compute a travel time and amplitude. If the experiment is over, the program proceeds along path 72 to calculate the gel strength from the amplitude data it previously stored.

Figure 6:
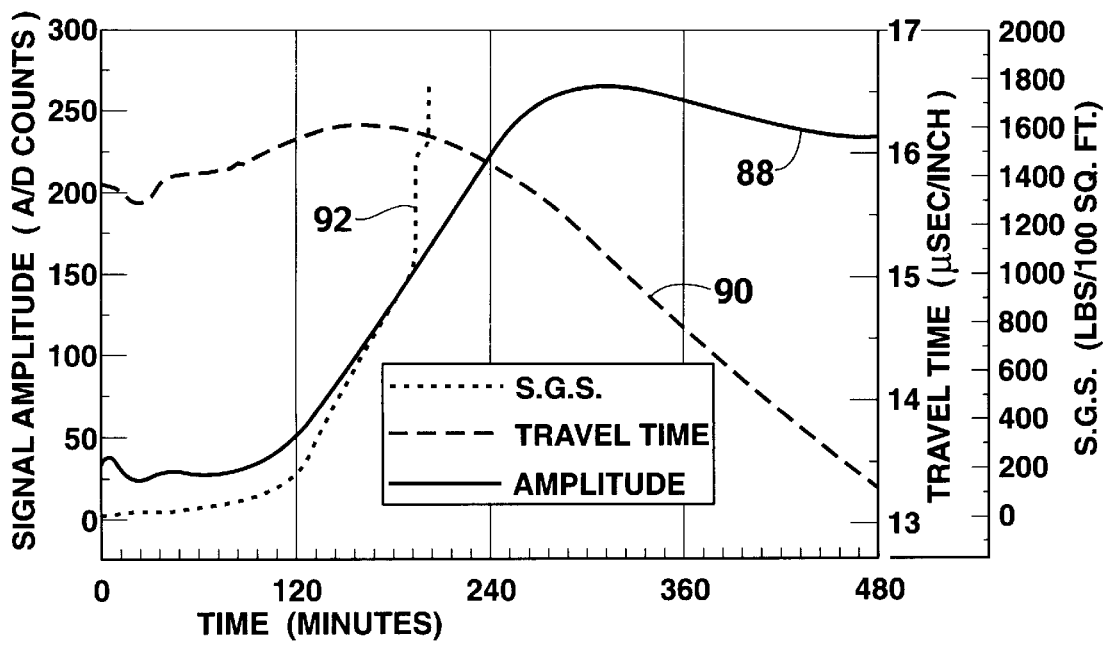
FIG. 6 is an exemplar cross plot of travel time and amplitude versus static gel strength.

The amplitude data is first filtered 74 with a low pass filter to remove any short duration changes in signal amplitude. This would appear as seen 20 minutes into the test shown in FIG. 6. The computer then searches the derivative of this filtered amplitude curve for the maximum positive derivative, step 76. In FIG. 6 this is at about 192 minutes. The maximum derivative corresponds to the maximum rate of gel strength development. It also coincidentally corresponds to a specific gel strength in all of the experimental data. The next step 78 is to reprocess the amplitude data with a low pass filter with a slightly higher cut off frequency. The derivative of this signal is then searched 80 for 0 derivative or 0 slope in the amplitude. The search starts from the time of the peak positive derivative and goes baqk in time to the first 0. In FIG. 6 several locations have 0 slope in the amplitude. The correct one is at 66 minutes into the test. Beginning the search at the time of maximum derivative and searching for the first zero prior to the maximum is important to obtaining the correct information. The time of the zero corresponds to the time in the experimental data that the gel strength consistently equaled 75 lbs./100 ft$^2$.

The next step in the process is to convert the amplitude data to gel strength. A linear relationship exists between the gel strength and the change in signal amplitude. The slope and intercept of the equation which converts the amplitude to gel strength are now calculated 82. The first requirement is that at the time of zero slope, the amplitude corresponds to 75 lbs./100 ft$^2$. The second requirement is that at the time of the maximum derivative the amplitude corresponds to 1200 lbs./100 ft$^2$. The slope and intercept are computed 84 allowing the gel strength to be computed for all points between the two times. The equation is not accurate outside these times. The gel strength data is then stored or plotted 86.

The travel time data may be used to compute compressive strength using techniques described by previous referenced patents.

In FIG. 6 the amplitude is indicated by the solid line 88, travel time by the dashed line 90 and measured static gel strength by the dotted line 92. The maximum derivative in amplitude occurs at about 192 minutes and the zero occurs at 66 minutes. The computed gel strength, therefore, would be 75 lbs./100 ft$^2$ at 66 minutes and 1200 lbs./100 ft$^2$ at 192 minutes. The gel strength shown is measured using the pressure drop test to determine gel strength. At the time the gel strength reaches 1200 lbs./100 ft$^2$, the method for computing compressive strength may be used since the travel time has now begun to decrease and the cement has reached initial set.

Though production versions of the program may vary somewhat in implementation, the basic processing of the signal will be approximately the same because the gel strength cannot be computed until the process is complete.

Figure 7:
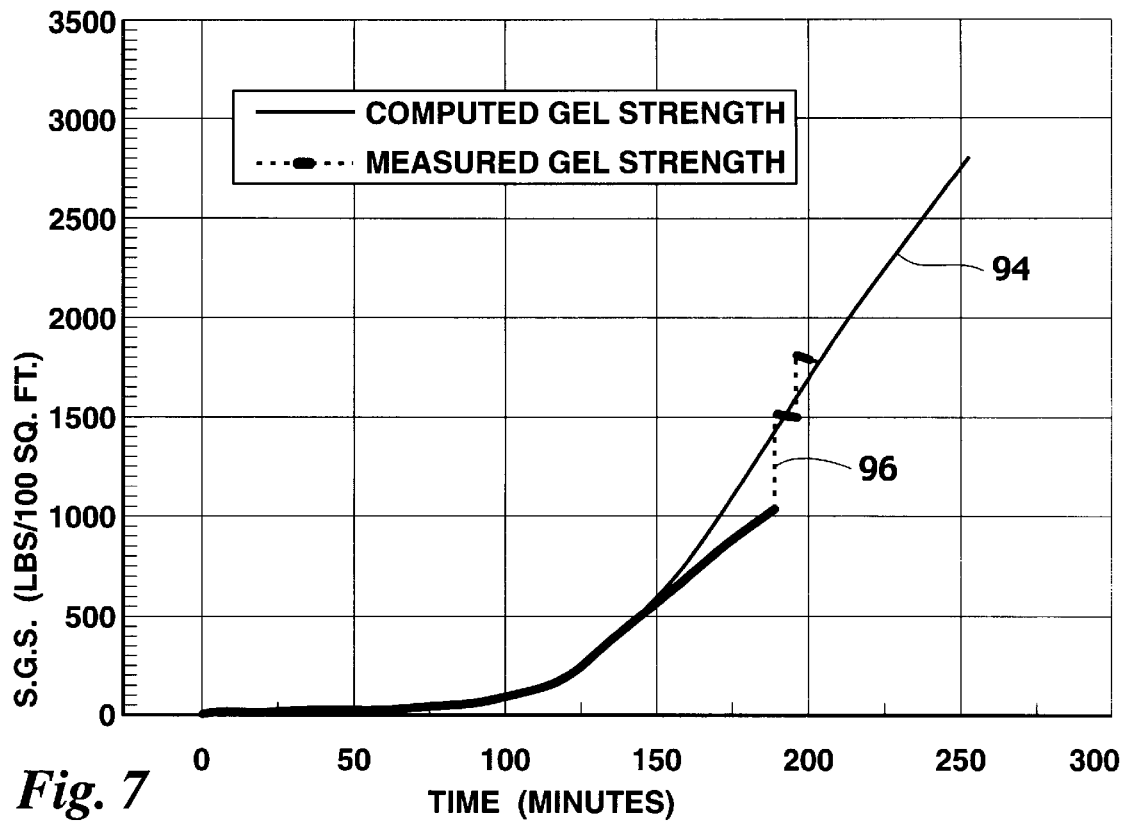
FIG. 7 is an exemplar cross plot of static gel strength over time comparing computed and measured values.

The following examples demonstrate the accuracy of the measurement. The result of utilizing this processing is shown in FIG. 7. This is same cement sample as is illustrated in FIG. 6. Processing the signal amplitude generates the solid line 94, the computed static gel strength. The comparative gel strength shown with dotted line 96 was measured using the pressure drop in a tube with constant flow rate. The processing of the amplitude data closely represents the development of gel strength in the cement sample. The gel strength at the minimum signal amplitude is 75 lbs/100 ft$^2$. The computed gel strength then closely approximates the measured gel strength up to 1200 lbs./100 ft$^2$.

Figure 8:
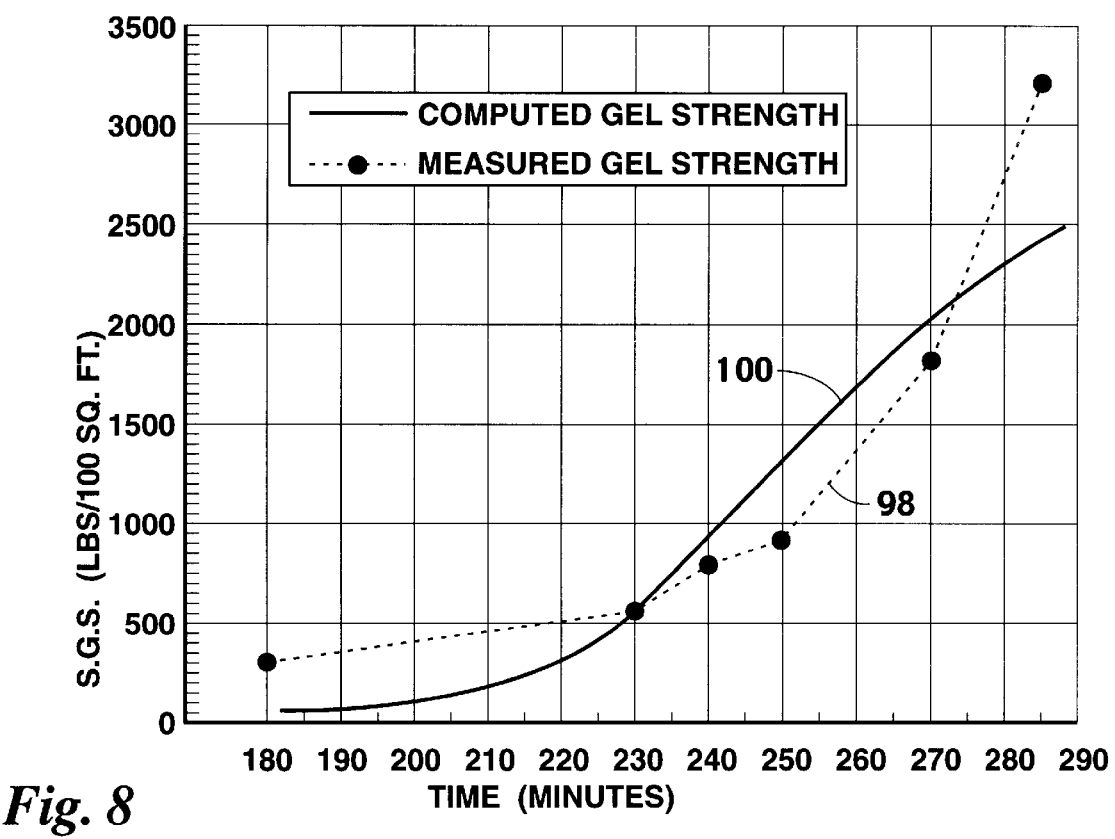
FIG. 8 is another exemplar cross plot of static gel strength over time comparing computed and measured values.

In order to further verify the accuracy of the gel strength measurement an alternate technique for measuring gel strength, the shearometer, was used in several experiments. In one experiment a 16 lb./gal. latex cement was tested. The modified UCA was operated at 3000 psi and at the same temperature as the shearometer measurement. The shearometer data is shown in FIG. 8 as a dashed line 98 with each measurement point marked. The gel strength computed from the processed amplitude data is shown as a solid line 100. Since individual samples are required for each measurement of gel strength, fewer measurements of the gel strength were made. The trend of the data is still accurate. This figure shows that the gel strength is very closely related to the signal amplitude regardless of the procedure for measuring gel strength. The gel strength computed from the signal amplitude accurately represents the measured gel strength until it reaches 2000 lbs./100 ft$^2$.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An acoustic method for determining the static gel strength of a cement slurry sample, comprising the steps of:
   (a) maintaining said sample in a static condition at a controlled temperature and pressure;
   (b) transmitting an acoustic signal through said sample;
   (c) measuring the amplitude of said acoustic signal as it transits said sample to obtain signal attenuation data;
   (d) repeating steps (b) and (c) at a predetermined number of time points, thereby producing a predetermined number of amplitude measurements;
   (e) calculating from said predetermined number of amplitude measurements at least one value representative of a derivative; and,
   (f) calculating a static gel strength of said sample by using at least one of said at least one values representative of a derivative.

2. The method according to claim 1 wherein said acoustic signal is an ultrasonic signal.

3. The method according to claim 2 wherein said ultrasonic signal is a high frequency signal in the range from about 100–600 kHz.

4. The method according to claim 1 further comprising pulsing said acoustic signal over time and repetitively performing steps (c) through (f) to obtain a time history of the static gel strength of said sample.

5. The method according to claim 1 further comprising comparing the static gel strength of said sample to an arbitrary value and determining the time when the static gel strength reaches said arbitrary value.

6. The method according to claim 5 wherein said arbitrary value represents the point at which signal amplitude begins to increase to indicate the onset of static gel strength development.

7. The method according to claim 5 wherein said arbitrary value represents the point at which signal amplitude reaches a maximum rate of increase to indicate a specific gel strength.

8. The method according to claim 1 wherein step (c) includes filtering said acoustic signal with a filter centered at 500 kHz to eliminate all frequencies outside a desired frequency range.

9. The method according to claim 1 further comprising simultaneously performing steps (a) through (c) upon multiple cement slurry samples and transmitting said signal attenuation data to a central processor which performs steps (d) through (f).

10. The method according to claim 1 further comprising simultaneously measuring the time required for said acoustic signal to transit said sample and determining the compressive strength of said sample using a predetermined relationship.

11. A system for determining the static gel strength of a cement slurry sample according to claim 1, comprising:
   (a) an acoustic pressure vessel to maintain said sample in a static condition at a controlled temperature and pressure;
   (b) a first transducer to transmit an acoustic signal through said sample;
   (c) a second transducer to record the amplitude of said acoustic signal after it transits said sample to obtain signal attenuation data; and
   (d) a data processor for determining the static gel strength of said sample according to the method of claim 1, wherein at least steps (e) and (f) of claim 1 are encoded as computer instructions with said data processor.

12. The system according to claim 11 wherein said first transducer is operable to transmit a high frequency ultrasonic acoustic signal in the range from about 100–600 kHz.

13. The system according to claim 11 further comprising a filter centered at 500 kHz to eliminate all frequencies outside a desired frequency range.

14. The system according to claim 11 further comprising a plurality of said acoustic pressure vessels and first and second transducers connected to said data processor to enable the simultaneous testing of multiple slurry samples.

15. A method for determining the static gel strength of a cement slurry sample, comprising the steps of:
   (a) maintaining said sample in a static condition at a controlled temperature and pressure;
   (b) transmitting an acoustic signal through said sample;
   (c) measuring the amplitude of said acoustic signal as it transits said sample to obtain signal attenuation data;

(d) repeating steps (b) and (c) at a predetermined number of time points to obtain a predetermined number of amplitude measurements and a same predetermined number of corresponding time points, said amplitude measurements and time points together comprising an amplitude curve;

(e) identifying, from within said amplitude curve, a region containing a plurality of amplitude measurements, wherein said amplitude curve is at least approximately linear; and, (f) using at least two of said amplitude measurements within said approximately linear region to calculate an estimate of said static gel strength.

16. A method according to claim 15, wherein step (f) includes the steps of:

(f1) selecting a first amplitude measurement from said at least two amplitude measurement, (f2) selecting a second amplitude measurement from said at least two amplitude measurements, (f3) calibrating a linear equation to said amplitude curve by associating a first predetermined static gel strength value with said first selected amplitude measurement, and, associating a second predetermined static gel strength value with said second selected amplitude measurement, and, (f4) estimating a static gel strength using said calibrated linear equation.

17. A method for determining the static gel strength of a cement slurry sample, comprising the steps of:

(a) maintaining said sample in a static condition at a controlled temperature and pressure;

(b) transmitting an acoustic signal through said sample;

(c) measuring an amplitude value of said acoustic signal as it transits said sample to obtain signal attenuation data;

(d) repeating steps (b) and (c) at a predetermined number of time points to obtain a predetermined number of amplitude values and a same predetermined number of corresponding time points, said amplitude values and time points together comprising an amplitude curve;

(e) identifying at least one amplitude value proximate to an inflection point of said amplitude curve;

(f) calculating a static gel strength of said sample by using at least one of said at least one amplitude values proximate to an inflection point.

18. A method according to claim 17, wherein step (f) includes the steps of:

(f1) selecting one of said at least one identified amplitude values, (f2) identifying a time point associated with said selected amplitude value, (f3) estimating a derivative of said amplitude curve for at least one time point different from said identified time point, (f4) choosing from among said at least one derivatives a maximum derivative, (f5) selecting a particular amplitude associated with said maximum derivative, (f6) calibrating a linear equation to said amplitude curve by associating a first predetermined static gel strength value with said selected identified amplitude value, and, associating a second predetermined static gel strength value with said selected particular amplitude value, and, (f7) estimating a static gel strength using said calibrated linear equation.

19. An acoustic method for determining the static gel strength of a cement slurry sample, comprising the steps of:

(a) maintaining said sample in a static condition at a controlled temperature and pressure;

(b) transmitting an acoustic signal through said sample;

(c) measuring the amplitude of said acoustic signal as it transits said sample to obtain signal attenuation data; and (d) calculating, according to a predetermined relationship relating signal attenuation to static gel strength, the static gel strength of said sample.

* * * * *